United States Patent [19]

Bitensky

[11] Patent Number: 5,476,764
[45] Date of Patent: Dec. 19, 1995

[54] METHOD USING CO FOR EXTENDING THE USEFUL SHELF-LIFE OF REFRIGERATED RED BLOOD CELLS

[75] Inventor: Mark W. Bitensky, Los Alamos, N.M.

[73] Assignee: The Regents of the University of California, Los Alamos, N.M.

[21] Appl. No.: 308,028

[22] Filed: Sep. 16, 1994

[51] Int. Cl.$^6$ .......................................................... A01N 1/02
[52] U.S. Cl. ................................................ 435/2; 424/533
[58] Field of Search .................................. 435/2; 424/533

[56] References Cited

U.S. PATENT DOCUMENTS 5,189,146  2/1993  Hsia ......................................... 530/385

FOREIGN PATENT DOCUMENTS 56-154418  11/1981  Japan .

OTHER PUBLICATIONS

Valeri C. R. in Blood Banking and the Use of Frozen Blood Products, CRC Press pp. 35–39 (1976).
Richard E. Waugh et al., "Rheologic Properties Of Senescent Erythrocytes: Loss Of Surface Area And Volume With Red Blood Cell Age," Blood 79, 1351 (1992).
Ken Ando et al., "Increased Susceptibiity Of Stored Erythrocytes To Anti–Band 3 IgG Autoantibody Binding," Biochimica et Biophysica Acta 1178, 127 (1993).
Phillip S. Low et al., "The Role Of Hemoglobin Denaturation And Band 3 Clustering In Red Blood Cell Aging," Science 227, 531 (1985).
Charles E. Huggins, "Frozen Blood; Principles of Practical Preservation," Monographs in the Surgical Sciences, 3, 133 (1966).
C. R. Valeri et al., "The Safety And Therapeutic Effectiveness Of Human Red Cells Stored At −80° C. For As Long As 21 Years," Transfusion 29, 429 (1989).
R. Blaine Moore et al., "Ascorbate Protects Against Tert–Butyl Hydroperoxide Inhibition Of Erythrocyte Membrane $Ca^{2+}$–+$Mg^{2+}$ATPase," Arch. Biochem. and Biophys. 278, 416 (1990).
Tanya Repka et al., "Hydroxyl Radical Formation By Sickle Erythrocyte Membranes: Role Of Pathologic Iron Deposits And Cytoplasmic Reducing Agents," Am. Soc. Hematology 10, 2753 (1991).
Eraldo Antonini et al., "Hemoglobin And Myoglobin In Their Reactions With Ligands," *Frontiers of Biology*, vol. 21, North–Holland Publishing Company, Amsterdam–London (1971).
J. McKenney et al., "Decreased In Vitro Survival Of Hydrogen Peroxide–Damaged Baboon Red Blood Cells," Blood 76, 206 (1990).

*Primary Examiner*—Marian C. Knode
*Assistant Examiner*—S. Saucier
*Attorney, Agent, or Firm*—Samuel M. Freund

[57] ABSTRACT

Method using CO for extending the useful shelf-life of refrigerated red blood cells. Carbon monoxide is utilized for stabilizing hemoglobin in red blood cells to be stored at low temperature. Changes observed in the stored cells are similar to those found in normal red cell aging in the body, the extent thereof being directly related to the duration of refrigerated storage. Changes in cell buoyant density, vesiculation, and the tendency of stored cells to bind autologous IgG antibody directed against polymerized band 3 IgG, all of which are related to red blood cell senescence and increase with refrigerated storage time, have been substantially slowed when red blood cells are treated with CO. Removal of the carbon monoxide from the red blood cells is readily and efficiently accomplished by photolysis in the presence of oxygen so that the stored red blood cells may be safely transfused into a recipient.

8 Claims, 5 Drawing Sheets

METHOD USING CO FOR EXTENDING THE USEFUL SHELF-LIFE OF REFRIGERATED RED BLOOD CELLS

FIELD OF THE INVENTION

The present invention relates generally to refrigerated storage of red blood cells and, more particularly, to the use of carbon monoxide for reversibly stabilizing the hemoglobin in red blood cells in order to extend the useful refrigerated storage lifetime thereof. This invention was made with government support under Contract No. W- 7405-ENG-36 awarded by the U.S. Department of Energy. The government has certain rights in the invention.

BACKGROUND OF THE INVENTION

Although the transfusion of human blood for elective surgery and trauma has been practiced for some 200 years, only recently have the extent of infectious and immunological risks and hazards of transfusions become more fully recognized. Transfusions are known to provoke immunological responses. That is, the recipient may reject the transfused cell, or more seriously, the transfused cells can immunologically reject the recipient. Additionally, transfusions can introduce viral pathogens including HIV as well as a spectrum of hepatotrophic viruses.

It is well known that red blood cells deteriorate during storage at 4° C. Recently, data have accumulated that show that the changes provoked by refrigerated storage are, in certain fundamental ways, similar to those found in normal red cell aging within the body. The extent and severity of these changes are directly related to the duration of refrigerated storage. Buoyant density increases and surface area decreases with accompanying vesiculation (loss of lipid-encapsulated vesicles from the surface of the red cell membrane). See, for example, Richard E. Waugh et al., "Rheologic Properties Of Senescent Erythrocytes: Loss Of Surface Area And Volume With Red Blood Cell Age," Blood 79, 1358 (1992). The vesicles formed at 4° C. appear to lack cytoskeletal proteins, and may contain concentrations of hemoglobin that are to some extent lower than those found in the red blood cell cytoplasm. Moreover, the tendency of stored red blood cells to bind autologous IgG antibody directed against polymerized band 3 increases with refrigerated storage time as is the case for aging red blood cells in vivo. See, for example, Ken Ando et al., "Increased Susceptibility Of Stored Erythrocytes To Anti-Band 3 IgG Autoantibody Binding," Biochimica et Biophysica Acta 1178, 127 (1993), and Philip S. Low et al., "The Role Of Hemoglobin Denaturation and Band 3 Clustering In Red Blood Cell Aging," Science 227, 531 (1985). Thus, it has become clear that, as hemoglobin begins to denature in vivo as well as in the refrigerator, it forms hemichromes that cross-link the cytosolic domain of the major erythrocyte membrane-spanning protein, band 3, into clusters. The extracellular projections of the band 3 clusters comprise the extracellular antibody recognition sites for antibodies directed against senescent red blood cells. In vivo, such antibody binding to the senescent red blood cells helps to trigger their removal from the circulation. See, for example, Low et al., supra. Ordinarily, refrigerated red cells are outdated and discarded by the end of week six since, by this time, as many as one-quarter of such transfused cells are rapidly removed from the circulatory system by the spleen of the transfusion recipient. The loss of stored red blood cells as a consequence of outdating may exceed one million units of blood each year within the continental United States alone.

There is an additional compelling need to develop technology for safely extending the storage life of red blood cells. A would-be autologous (patient-to-self) donor cannot provide a unit of blood for storage more often than about once every two weeks without seriously depleting the body's existing red blood cell cadre. Because blood can be safely stored only for five to six weeks, by the time a patient is able to donate a third or fourth unit, the first unit collected would already have begun to deteriorate. Thus, in practice, an individual may safely donate three to four units of blood to his or her own account; however, there are many frequently performed surgical procedures that require more than 14 units of blood, especially those which require extracorporeal support for the circulation and oxygenation of blood.

Currently, red blood cells are stored in the presence of adenine and glucose using, in addition, a variety of soluble salts including such cations as magnesium, sodium, and potassium and such anions as chloride and citrate, which prevent hemolysis as well as cell clumping and coagulation of serum proteins. However, the refrigeration-associated changes including loss of membrane surface area, vesicle formation, and an increase in susceptibility to autologous antibody binding against band 3, as well as an increase in buoyant density that are mentioned above, are not adequately prevented by current practices and procedures.

Red blood cells are also stored in the frozen state, either in the presence of glycerol or in the presence of dimethylsulfoxide. See, for example, Charles E. Huggins, "Frozen Blood: Principles Of Practical Preservation," Monograph In The Surgical Sciences 3, 133 (1966). The use of dimethylsulfoxide has been banned in the United States because of its toxicity and because it also causes hemolysis as well as subtle damage to red blood cell membrane structures. Glycerol is currently used for freezing red blood cells, especially by the military. See, for example, C. R. Valeri et al., "The Safety And Therapeutic Effectiveness Of Human Red Cells Stored At −80° C. For As Long As 21 Years," Transfusion 29, 429 (1989). However, methods employing glycerol are expensive, labor intensive, cumbersome, and are also associated with non-trivial red blood cell losses. Moreover, red blood cells that have been frozen in glycerol must be cleansed of this material after thawing by a slow, labor-intensive process, and have a relatively short useful half-life once thawed, during which time they must be transfused or discarded.

Hemin and hemichrome (decomposition products of hemoglobin) have been suspected of having the capability to function as cell membrane-damaging agents. Hemichrome is now known specifically to cause polymerization of the red cell anion channel (band 3) in vivo, resulting in disorganization of the red cell membrane cytoskeleton and loss of connections between the cytoskeletal fibers and the lipid bilayer. See, for example, Low et al., supra. Hemin (formed from hemichrome) and $Fe^{3+}$, which is formed from Hemin, act as catalysts for oxygen radical formation and subsequent damage to hemoglobin, the membrane cytoskeleton, and the lipid bilayer.

It has recently become apparent that cumulative oxidative damage is a limitation on the useful storage life of refrigerated red blood cells. Much research has recently been focused on the design and incorporation of antioxidants into the storage medium. These include analogues of reduced glutathione, vitamin C, and vitamin E. Overall, the advantages provided by such additions have been found to be modest. See, for example, R. Blaine Moore et al., "Ascorbate Protects Against tert-Butyl Hydroperoxide Inhibition Of Erythrocyte Membrane $Ca^{2+}+Mg^{2+}$-ATPase," Arch. Biochem. and Biophys. 278, 416 (1990). Interestingly, in Tanya Repka et al., "Hydroxyl Radical Formation By Sickle Erythrocyte Membranes: Role Of Pathologic Iron Deposits And Cytoplasmic Reducing Agents," Am. Soc. Hematology 10, 2753 (1991 ), the authors find that administration of pharmacological amounts of ascorbic acid to sickle disease patients may be potentially hazardous due to adversely tipping the delicate antioxidant/pro-oxidant balance, since their results indicate that ascorbate can have both antioxidant and pro-oxidant effects.

There have also been a number of attempts to develop "blood substitutes" where hemoglobin can be delivered to patients in a stabilized form as a substitute for intact red blood cells. As an example, in Jen-Chang Hsia, "Pasteurizable Freeze-Driable Hemoglobin-Based Blood Substitute," U.S. Pat. No. 5,189,146, which issued on Feb. 23, 1993, hemoglobin is stabilized in its tetrameric form. This composition is prepared by diluting whole blood with isotonic NaCl solution and filtering it to separate the red blood cells from the plasma. The red blood cells are then washed in isotonic saline and lysed with hypotonic phosphate buffer. Particulate matter is separated from soluble hemoglobin by filtration. Cell-free oxyhemoglobin is converted to deoxyhemoglobin by applying a vacuum or by gas exchange in the presence of a reducing agent. The resulting deoxyhemoglobin is stabilized by the addition of a cross linker that stabilizes a specific conformation in monomeric or polymeric conjugates. The stabilized compound is then washed and concentrated, carbon monoxide is added, and the material is subsequently pasteurized at 60° C. for 10 hours. Both liquid solutions and dry powders of CO-stabilized cross-linked hemoglobins were found to be quite stable to long term storage at moderate temperatures (for example, 56° C. for 60 days).

Removal of CO under aseptic conditions is a prerequisite for use of cross-linked hemoglobins as a blood substitute. Hsia teaches that the CO-stabilized product can readily be photoconverted in the presence of oxygen to the oxygenated derivative oxy-hemoglobin which is suitable for transfusion. This material finds application as a blood plasma expander for use in acute emergencies, but has a circulatory half-life of only 4–5 hours.

In this context, the capacity of visible light to efficiently photolyze carbon monoxide hemoglobin derivatives has been known for many years. In Eraldo Antonini et al., "Hemoglobin And Myoglobin In Their Reactions With Ligands," *Frontiers Of Biology*, Vol. 21, North-Holland Publishing Company, Amsterdam-London (1971), the chemistry of carbon monoxide derivatives of hemoglobin and myoglobin is discussed in detail, including the photochemistry thereof.

Carbon monoxide has also been used to reduce the membrane damage that is induced in red blood cells by $H_2O_2$. In J. McKenney et al., "Decreased In Vitro Survival Of Hydrogen Peroxide-Damaged Baboon Red Blood Cells," Blood 76, 206 (1990), the authors observed that exposure of human red blood cells to low concentrations of hydrogen peroxide in vitro results in membrane damage as manifested by the generation of spectrin-hemoglobin complexes, decreased red blood cell deformability, and cell surface alterations. Moreover, such exposures to $H_2O_2$ lead to enhanced phagocytosis of the oxidized cells by monocytes. Prior treatment with carbon monoxide, however, completely inhibited cellular alterations induced by the $H_2O_2$, and, in particular, the formation of the spectrin-hemoglobin complexes. Because of their biophysical and post-transfusion survival characteristics, baboon red blood cells are considered to be a reasonable surrogate for human red blood cells. McKenney et al. do not, however, suggest or demonstrate the efficacy of the application of hemoglobin/red blood cell stabilization by hemoglobin ligand such as CO for the purpose of extending the useful shelf-life of refrigerated red blood cells.

It is clear that prevention of the formation of hemichrome and its toxic derivatives is preferable to attempts to minimize the damage that these species are capable of producing, once they have formed. However, to date there have been no applications of hemoglobin/red blood cell stabilization techniques using hemoglobin-stabilizing ligands applied to prolonging the useful shelf-life of refrigerated red blood cells.

Accordingly, it is an object of the present invention to substantially prolong the survival of refrigerated red blood cells in a manner consistent with the practice of autologous transfusion.

Another object of the subject invention is to prolong the survival of refrigerated red blood cells without the necessity for complex or labor intensive procedures to generate transfusible samples.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for prolonging the useful life of refrigerated storage of red blood cells includes the steps of introducing a sample of whole blood into a sealed pouch that contains an isotonic anticoagulant, thereby forming a first suspension, sedimenting the first suspension, whereby a major portion of the liquid fraction (plasma) is separated from the red blood cells to be stored, thereby forming a mass of packed red blood cells which retains a small amount of the original plasma, adding a solution containing citrate, phosphate, various salts, glucose, and adenine to the packed red blood cells, thereby forming a second suspension, cooling the second suspension to about 4° C., and exposing the cooled, second suspension to sufficient CO to substantially stabilize all of the hemoglobin molecules present in the red blood cells to be stored.

It is preferred that the second suspension be fully saturated with carbon monoxide, and that the environment in contact with the second suspension contain carbon monoxide.

It is also preferred that the carbon monoxide is sterilized before said step of adding carbon monoxide to the first suspension.

It is further preferred that the carbon monoxide in contact with the second suspension be changed either initially and/or from time-to-time in order to maximize and/or achieve the desired hemoglobin saturation with carbon monoxide consistent with obtaining a maximum degree of hemoglobin stabilization.

Preferably, the carbon monoxide is removed from the second suspension immediately prior to the time that it is desirable to transfuse the stored red blood cells, by a photolyric step involving irradiation of the red blood sample using light having wavelengths between 260 and 480 nm.

It is preferred that during the photolyric step, the blood is caused to form a thin film such that the optical density of the second suspension is low.

Preferably also, during the photolytic step, oxygen is added to the second suspension.

Benefits and advantages of the present invention include the reduction of red blood cell damage by stabilizing the hemoglobin therein, thereby reducing exposure of the stored red blood cells to hemichrome, Hemin, $Fe^{3+}$, oxygen radicals, and other species harmful to the cell membrane with the result that useful refrigerated storage periods may be prolonged. Thus, each individual is thereby enabled to serve as an autologous donor for the purpose of elective surgical procedures, and would be able to gradually accumulate red blood cell units for such transfusions for extended periods of time. This would eliminate the need for blood typing and cross-matching as well as screening blood samples for infectious agents. The present invention would thus increase the scope and utility of the blood supply since there would be a decrease in infectious risk, mismatching accidents, immunological incompatibilities, and the cost per unit transfused as well as a decrease in the incidence of discarding outdated units. Moreover, the benefits mentioned above would improve the logistics of heterologous (donor to other) transfusion.

BRIEF DESCRIPTION OF THE DRAWINGS

The accompanying drawings, which are incorporated in and form a pad of the specification, illustrate one embodiment of the present invention and, together with the description, sere to explain the principles of the invention. In the drawings.

DETAILED DESCRIPTION OF THE INVENTION

Briefly, the present invention includes the use of carbon monoxide for stabilizing hemoglobin in red blood cells to be stored at about 4° C. A number of indicia of red cell health indicate that the useful life of such cells is significantly improved. These indicia include, but are not limited to, the extent of vesicle formation, buoyant density gradient analysis on discontinuous Stractan gradients, and the binding of autologous antibodies. Therefore, red blood cell storage by refrigeration in the hospital and blood bank environment may be significantly improved. The method will be especially valuable for autologous blood donations by elective surgery patients, especially when more than four units of blood are needed. The CO can be quantitatively removed by photolysis of the stabilized red blood cell sample in the presence of oxygen, immediately prior to the transfusion of a given unit of blood. Significant advantages may accrue from the pooling of many units of blood for the purpose and during the process of purging carbon monoxide.

Presently, refrigerated blood must be transfused to recipients within six weeks of donation. For periods of time greater than this, extensive deterioration resulting in reduced survival times will certainly occur in the red blood cells stored at 4° C. The damage manifests itself as hemichrome-induced changes in the organization of the cytoskeleton, as oxygen radical damage to the red blood cell membrane proteins and lipids, and as damage to a variety of membrane protein structures, especially those linking the lipid bilayer to the cytoskeleton. A reduced-oxygen atmosphere has been found to be somewhat helpful, and can be partially achieved by equilibrating the stored red blood cells with inert gases. However, nitrogen or argon do not stabilize hemoglobin in the manner observed with carbon monoxide, since the inert gases merely displace the oxygen, rather than functioning as true ligands of hemoglobin. It is believed that effective refrigerated red blood cell life may be extended for periods of six or more months using the present method that combines hemoglobin stabilization with carbon monoxide in the same step as oxygen removal.

Figure 1:
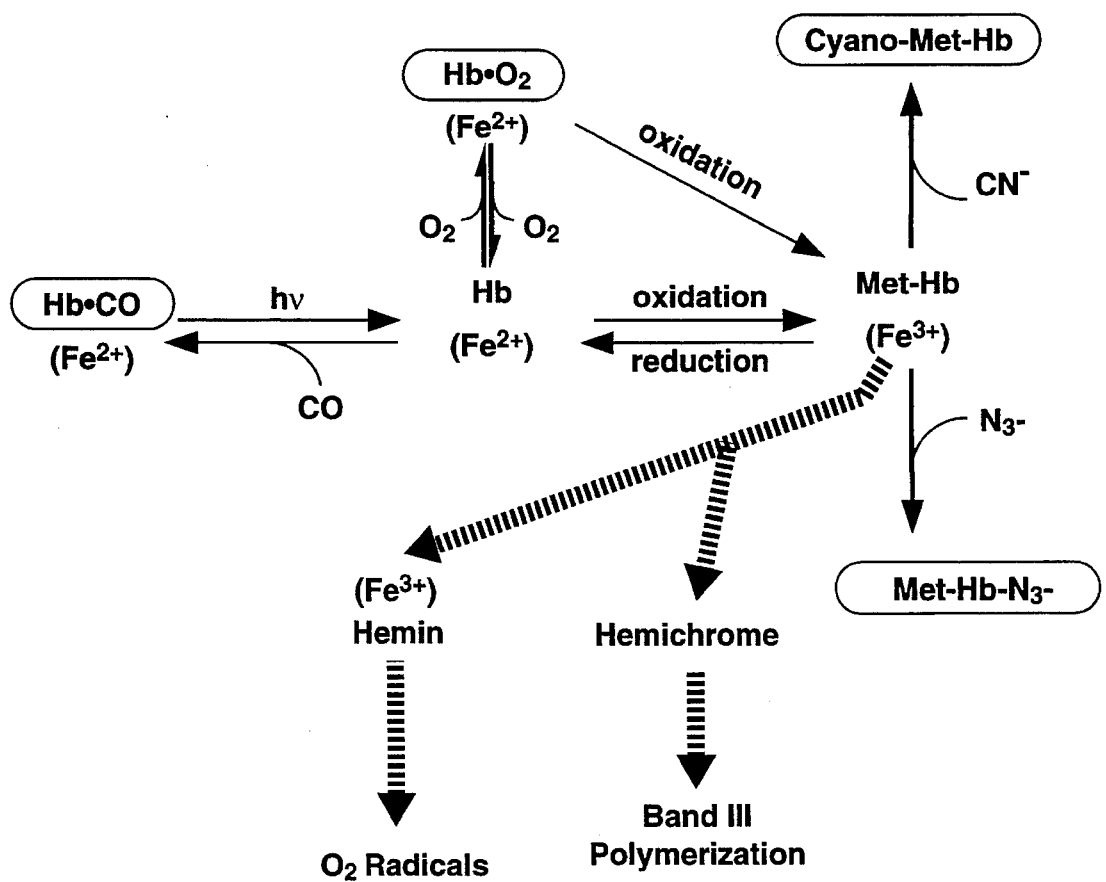
FIG. 1 shows the important ligand interactions of hemoglobin as well as the degradation pathway to form hemichrome from methemoglobin and, in particular, illustrates the stabilization of methemoglobin by azide or cyanide, and the stabilization of hemoglobin by carbon monoxide, either stabilization significantly reducing the undesirable formation of hemichrome and hemin from methemoglobin.

Reference will now be made in detail to the present preferred embodiments of the invention, examples of which are illustrated in the accompanying drawings. Turning now to the drawings, FIG. 1 shows the important ligand interactions of hemoglobin as well as the degradation pathway to form hemichrome from methemoglobin and, in particular, illustrates the stabilization of methemoglobin by azide or cyanide, and the stabilization of hemoglobin by carbon monoxide, either stabilization significantly reducing the undesirable formation of hemichrome and hemin from methemoglobin, and leading to a significant prolongation of the useful shelf-life of refrigerated stored red blood cells as will be described hereinbelow.

Having generally described the invention, the following specific example is given as a further illustration thereof.

EXAMPLE

Human whole blood samples (about 500 ml) were drawn from healthy, informed volunteer donors into a plastic pouch containing citrate, phosphate, sodium chloride, and dextrose (anticoagulant/buffer solution). The solution and pouch were obtained commercially (Miles, Inc.). The first solution to which whole blood was added was present in a volume ratio of 1 part anticoagulant solution to 7 parts of whole blood. After centrifugation at 1500 g for 10 min., the plasma was removed, and a second, similar solution (this second solution contained the additional component, adenine) was added to the remaining packed red blood cells such that the resuspended cells had a hematocrit of about 65. Four sets of samples were prepared:

A. Control samples were prepared by adding the above-described commercially available anticoagulant/buffer solution, as well as saturating the space above the red blood cells in the pouch with argon.

B. $NaN_3$-stabilized red blood cell samples were prepared by adding the above-described commercially available anticoagulant/buffer solution plus $NaN_3$ to make a 5 mM solution in azide.

C. For samples containing CO stabilized red blood cells, CP Grade CO was delivered into the pouch where the anticoagulant/buffer solution was chilled to 4° C. After gentle shaking for 2–6 hours the gas phase was exhausted from the pouch, and fresh CO was added in order to expel the residual oxygen, and saturate the sample with CO. This latter procedure may be repeated in order to ensure CO saturation. Samples were stored in plastic blood pouches in a blood bank refrigerator at 4° C.

D. Potassium cyanide was added to some of the samples prepared under method C. above.

On a regular basis, small aliquots were removed with sterile precautions through a multi-injector port inserted into the pouch, and tested for three indicia of red blood cell status.

Figure 2:
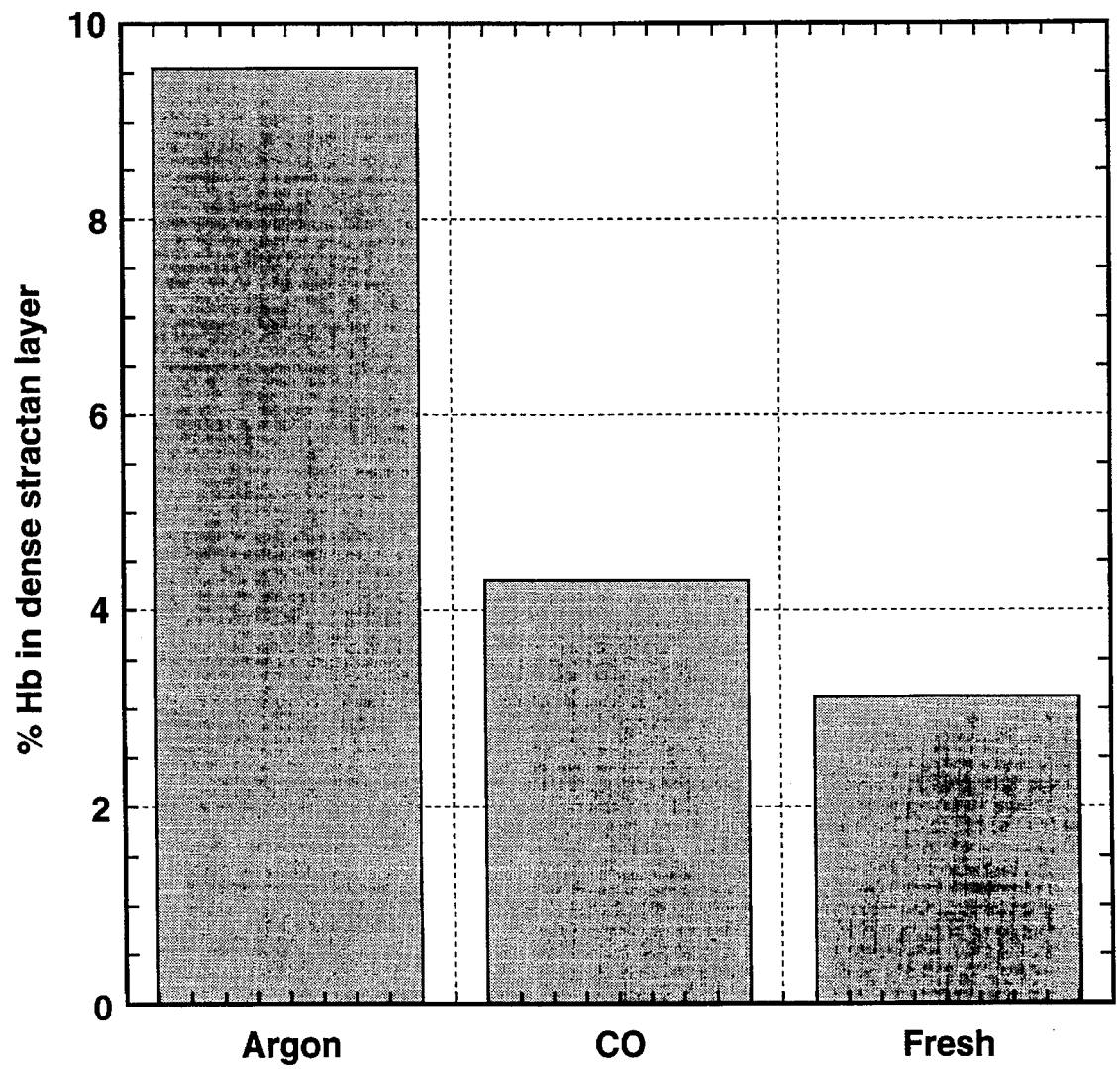
FIG. 2 is a bar graph illustrating the percentage of red blood cells that enter an arbitrarily chosen dense Stractan centrifugation layer for red blood cells stored under argon for 13 days, after treatment with carbon monoxide and storage for 13 days, and for a fresh sample of red blood cells.

Buoyant density was measured on purified discontinuous Stractan, arabin-oglycan 22–32% gradients (295–300 mosmol/kg). Quantitative measurements of cell density and distribution of centrifugation density were performed using a Beckman gel densitometry absorption scanner at 600 nm from film negatives of the density gradients. The results are illustrated in FIG. 2 where the amount of hemoglobin is measured from red blood cells that enter an arbitrarily chosen Stractan layer for red blood cells stored for 13 days under argon or carbon monoxide. Comparison is made with a fresh blood sample. FIG. 2 indicates that carbon monoxide (as compared with argon) reduces the rate at which storage-related processes increase the buoyant density of refrigerated red blood cells. That is, increased buoyant density found in the refrigerated red blood cells stored under argon upon density centrifugation in the discontinuous Stractan gradient, indicates progressive deterioration or aging of the red cells. It is known that as red blood cells get older they lose surface area and attain higher density. In a typical Stractan density gradient analysis, the younger cells stay closer to the top layers and older cells gravitate toward the bottom. The densitometry data correspond well with findings in the qualitative studies under the microscope. In experiments comparing cells stored for different time periods, different populations of red cells were separated in the Stractan gradients. Very young cells (reticulocytes) were found in the more buoyant fractions of the density gradients and few, if any, were observed in the denser fractions.

Figure 3:
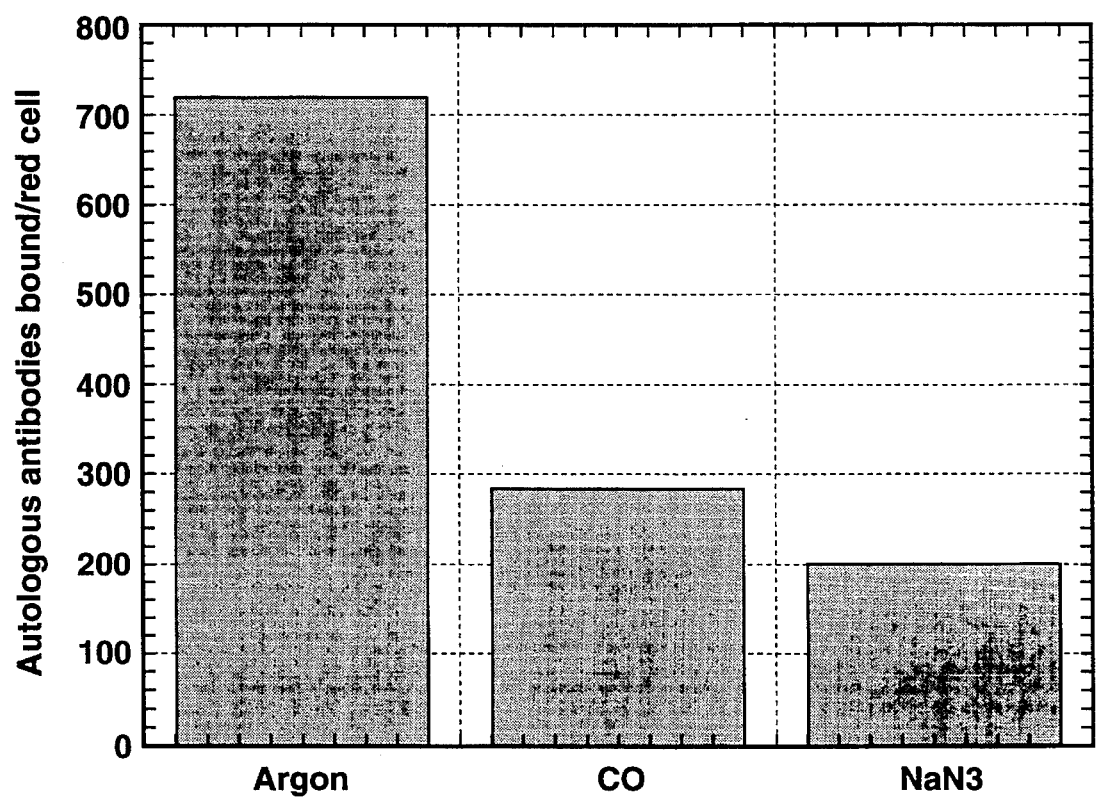
FIG. 3 is a bar graph illustrating autologous antibodies bound per red blood cell for red blood cells stored for 35 days in the presence of argon, carbon monoxide, and sodium azide.
Figure 4:
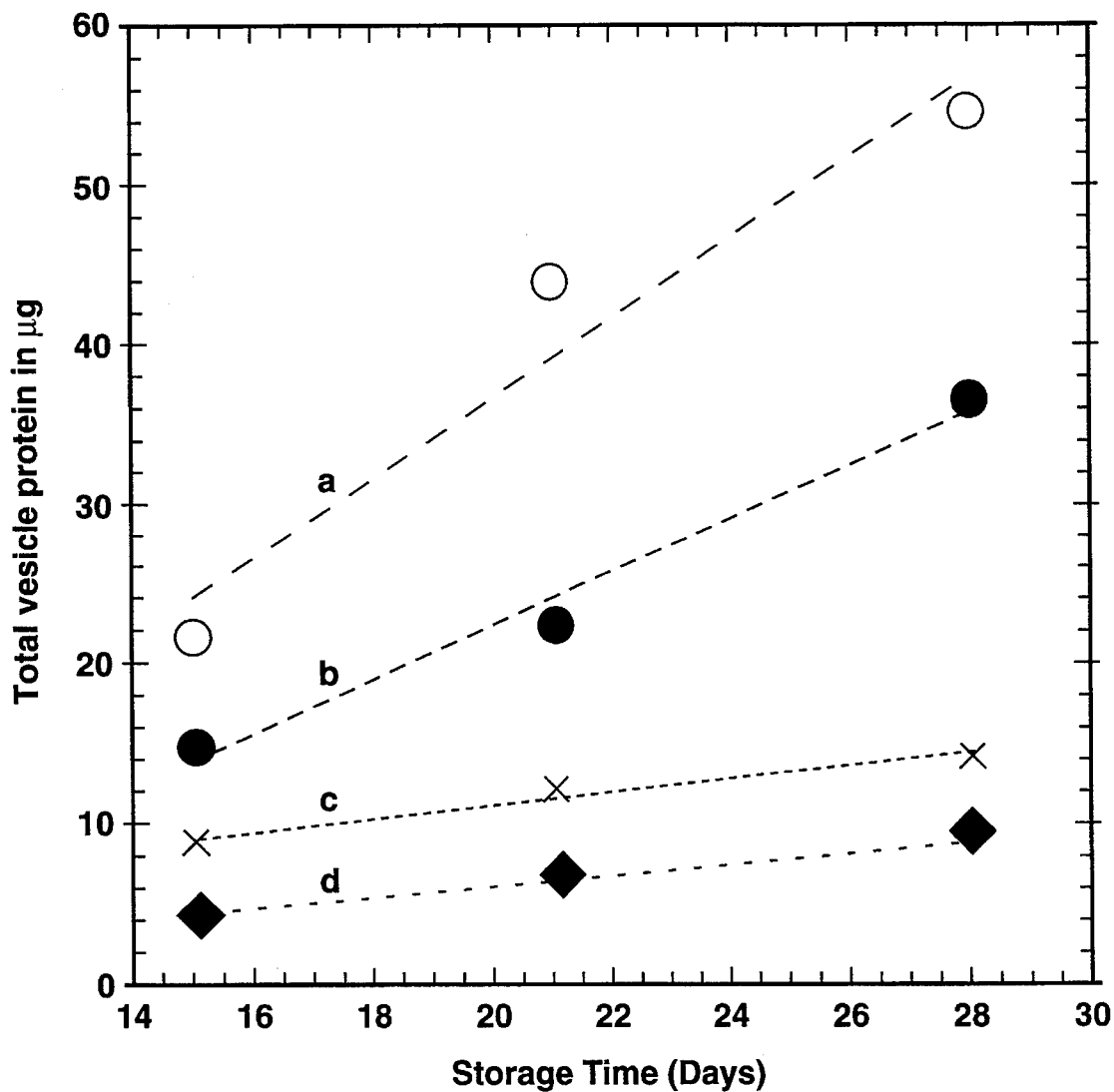
FIG. 4 is a plot . . . in the presence of (a) oxygen, (b) argon, (c) carbon monoxide, or (d) carbon monoxide plus cyanide.

FIG. 3 illustrates autologous antibodies bound per red blood cell for red blood cells stored for 35 days in the presence of argon, carbon monoxide, and sodium azide. Here, carbon monoxide and azide interfere with hemichrome-induced changes in band 3 that increase the binding of autologous antibody. Clearly, sodium azide protects the hemoglobin more strongly than carbon monoxide. However, azides cannot readily be removed from the stored blood for transfusion into a recipient, while CO, which affords excellent protection, is readily removed by photolysis.

FIGS. 4a–4d are plots of the total vesicle protein shed from the red blood cell body as a function of the number of storage days in the presence of oxygen, argon, carbon monoxide, or carbon monoxide plus cyanide, respectively. To be noticed is that a mixture of CO with sodium cyanide protects the hemoglobin more strongly than pure CO. Again, however, cyanides are much too difficult to remove from the stored blood for transfusion purposes.

Figure 5:
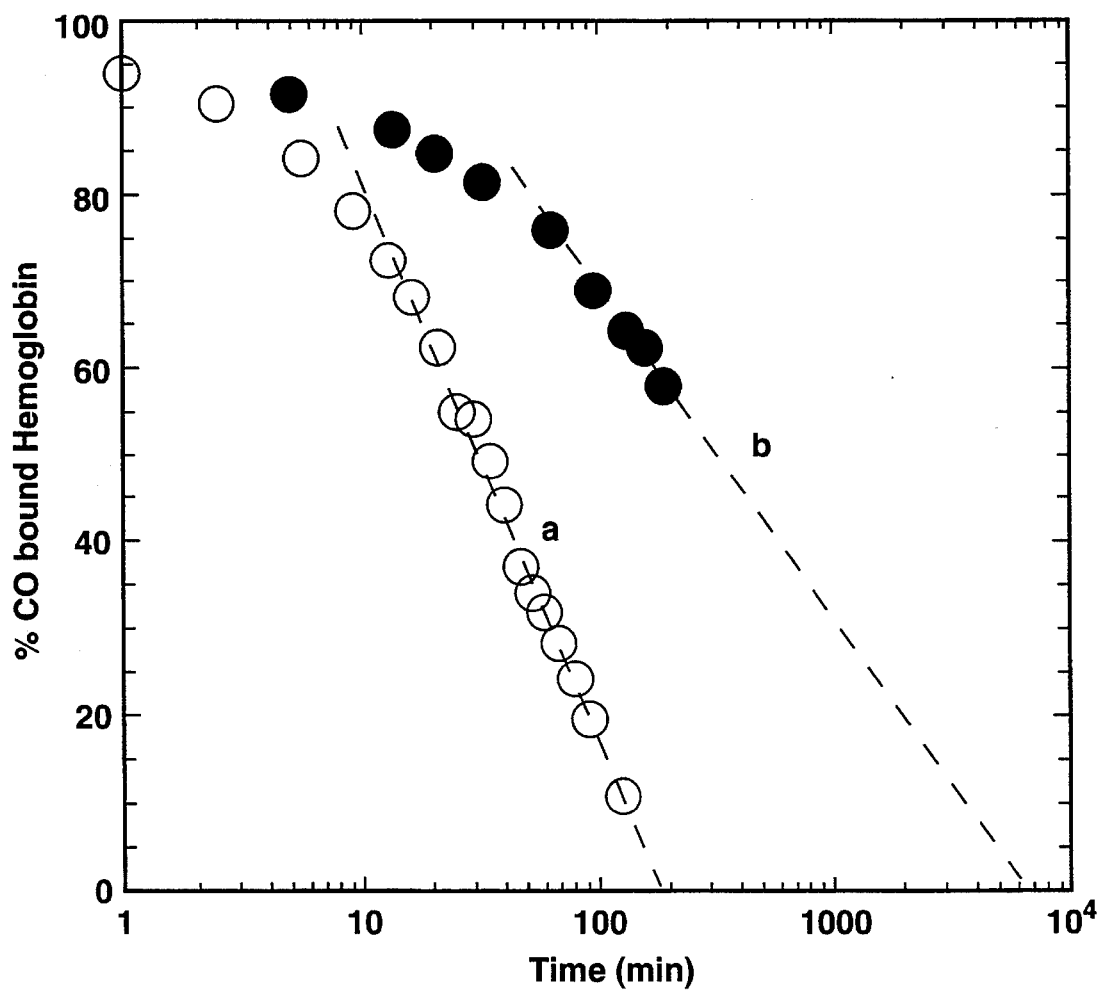
FIG. 5 is a plot . . . photolysis (a) in the presence of oxygen, and (b) in the presence of oxygen with no light present.

FIGS. 5a and 5b demonstrate the removal of carbon monoxide from a bulk sample of red blood cells by photolysis using a 500 W halogen lamp in the presence of oxygen, and in the presence of oxygen with no light present, respectively. It is seen that CO may be quantitatively removed from red blood cells. The lengthy irradiation time required to reduce the CO level to less than 10% is the result of the simple procedure employed. Since red blood cells are effectively opaque to incident light, only the surface layer is processed at a given moment. By reducing the optical path length of the incident radiation, rapid processing and virtually complete removal of CO will be able to be achieved. It should be mentioned that smokers commonly exhibit 1–5% carbon monoxyhemoglobin in their blood. See, for example, Eraldo Antonini and Maurizio Brunori, supra.

The foregoing description of the invention has been presented for purposes of illustration and description and is not intended to be exhaustive or to limit the invention to the precise form disclosed, and obviously many modifications and variations are possible in light of the above teaching.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for storing red blood cells which consists essentially of the steps of:.

a. mixing a sample of whole blood containing the red blood cells to be stored with a first anticoagulant solution, forming thereby a first suspension of red cells;

b. concentrating the red blood cells from the first suspension, forming thereby packed red blood cells;

c. mixing the packed red blood cells so produced with a second anticoagulant solution which comprises glucose, adenine, and salts, forming thereby a second suspension of red blood cells;

d. cooling the second suspension of red blood cells to 4° C.; and e. introducing carbon monoxide into the cooled second suspension of red blood cells and maintaining a sufficient quantity thereof such that the hemoglobin in the red blood cells is substantially stabilized thereby.

2. The method as described in claim 1, wherein the cooled second suspension of red blood cells is stored as a saturated solution of carbon monoxide.

3. A method for storing red blood cells which consists essentially of the steps of:

a. forming a quantity of packed red blood cells;

b. mixing the packed red blood cells with an anticoagulant solution which comprises glucose, adenine, and salts, forming thereby a suspension of red blood cells;

c. cooling the suspension of red blood cells to 4° C.; and d. introducing carbon monoxide into the cooled suspension of red blood cells and maintaining a sufficient quantity thereof such that the hemoglobin in the red blood cells is substantially stabilized thereby.

4. The method as described in claim 3, wherein the cooled suspension of red blood cells is stored as a saturated solution of carbon monoxide.

5. A method for storing red blood cells which consists essentially of the steps of:
   a. mixing a sample of whole blood containing the red blood cells to be stored with a first anticoagulant solution, forming thereby a first suspension of red cells;
   b. concentrating the red blood cells from the first suspension, forming thereby packed red blood cells;
   c. mixing the packed red blood cells so produced with a second anticoagulant solution which comprises glucose, adenine, and salts, forming thereby a second suspension of red blood cells;
   d. cooling the second suspension of red blood cells to 4° C.;
   e. introducing carbon monoxide into the cooled second suspension of red blood cells and maintaining a sufficient quantity thereof such that the hemoglobin in the red blood cells is substantially stabilized thereby; and
   f. illuminating the cooled second suspension of red blood cells containing carbon monoxide with light having wavelengths between 260 and 480 nm to drive off the carbon monoxide before use thereof.

6. A method for storing red blood cells which consists essentially of the steps of:
   a. mixing a sample of whole blood containing the red blood cells to be stored with a first anticoagulant solution, forming thereby a first suspension of red cells;
   b. concentrating the red blood cells from the first suspension, forming thereby packed red blood cells;
   c. mixing the packed red blood cells so produced with a second anticoagulant solution which comprises glucose, adenine, and salts, forming thereby a second suspension of red blood cells;
   d. cooling the second suspension of red blood cells to 4° C.;
   e. introducing carbon monoxide into the cooled second suspension of red blood cells and maintaining a sufficient quantity thereof such that the hemoglobin in the red blood cells is substantially stabilized thereby;
   f. illuminating the cooled second suspension of red blood cells containing carbon monoxide with light having wavelengths between 260 and 480 nm to drive off the carbon monoxide before use thereof; and
   g. introducing oxygen into the cooled second suspension of red blood cells containing carbon monoxide during said step of illumination thereof in order to assist in driving the carbon monoxide from the red blood cells.

7. A method for storing red blood cells which consists essentially of the steps of:
   a. forming a quantity of packed red blood cells;
   b. mixing the packed red blood cells with an anticoagulant solution which comprises glucose, adenine, and salts, forming thereby a suspension of red blood cells;
   c. cooling the suspension of red blood cells to 4° C.;
   d. introducing carbon monoxide into the cooled suspension of red blood cells and maintaining a sufficient quantity thereof such that the hemoglobin in the red blood cells is substantially stabilized thereby; and
   e. illuminating the cooled suspension of red blood cells containing carbon monoxide with light having wavelengths between 260 and 480 nm to drive off the carbon monoxide before use thereof.

8. A method for storing red blood cells which consists essentially of the steps of:
   a. forming a quantity of packed red blood cells;
   b. mixing the packed red blood cells with an anticoagulant solution which comprises glucose, adenine, and salts, forming thereby a suspension of red blood cells;
   c. cooling the suspension of red blood cells to 4° C.;
   d. introducing carbon monoxide into the cooled suspension of red blood cells and maintaining a sufficient quantity thereof such that the hemoglobin in the red blood cells is substantially stabilized thereby;
   e. illuminating the cooled suspension of red blood cells containing carbon monoxide with light having wavelengths between 260 and 480 nm to drive off the carbon monoxide before use thereof; and
   f. introducing oxygen into the cooled second suspension of red blood cells containing carbon monoxide during said step of illumination thereof in order to assist in driving the carbon monoxide from the red blood cells.

\* \* \* \* \*